US008465930B2

(12) United States Patent
Inokuchi

(10) Patent No.: US 8,465,930 B2
(45) Date of Patent: Jun. 18, 2013

(54) METHOD FOR DETECTION OF DISEASE HAVING INSULIN-RESISTANT CONDITIONS

(75) Inventor: Jinichi Inokuchi, Miyagi (JP)

(73) Assignee: Japan Science and Technology Agency, Saitama (JP)

( * ) Notice: Subject to any disclaimer, the term of this patent is extended or adjusted under 35 U.S.C. 154(b) by 362 days.

(21) Appl. No.: 12/301,997

(22) PCT Filed: May 29, 2007

(86) PCT No.: PCT/JP2007/061246
§ 371 (c)(1),
(2), (4) Date: Jun. 17, 2010

(87) PCT Pub. No.: WO2007/139224
PCT Pub. Date: Dec. 6, 2007

(65) Prior Publication Data
US 2010/0273192 A1    Oct. 28, 2010

(30) Foreign Application Priority Data

May 30, 2006   (JP) ................................. 2006-149328

(51) Int. Cl.
*G01N 33/53*   (2006.01)
(52) U.S. Cl.
USPC .......................................... 435/7.1; 436/518
(58) Field of Classification Search
None
See application file for complete search history.

(56) References Cited

U.S. PATENT DOCUMENTS

2007/0161586 A1   7/2007 Fuse

FOREIGN PATENT DOCUMENTS

| JP | 62-187254 | 8/1987 |
| JP | 2005-221293 | 8/2005 |
| JP | 2005-253434 | 9/2005 |
| WO | 2005/067971 | 7/2005 |
| WO | WO 2005/108600 | 11/2005 |

OTHER PUBLICATIONS

Guthmann et al. (J. Immunother. 2004 vol. 27, p. 442-451).*
Rebbaa et al. J. Lipid Res. 1995 vol. 36, p. 564-572.*
Tadashi Yamashita, et al.: "Enhanced insulin sensitivity in mice lacking ganglioside GM3", Proceeding of the National Academy of Sciences of the United States of America, Mar. 18, 2003, vol. 100(6), pp. 3445-3449.
Jin'ichi Inokuchi, et al.: "Micro Domain Syndrome to shite no Insulin Teikosei to 2-Gata Tonyobyo", Protein, Nucleic acid and Enzyme, 2003 Nen 6 Gatsu 10 Nichi Hakko, vol. 48(8), pp. 1179-1183.
R. Ziegler, et al.: "Multiple Target Antigens in Pre-type 1 Diabetes: Implications for Prediction", Hormone Research, Aug. 1990, vol. 33(2/4), pp. 144-151.
Jin'ichi Inokuchi: Micro Domain Byo to shite no Insulin Teikosei: Ganglioside GM3 no Kan'yo, Dai 53 Kai The Society of Polymer Science, Japan Toronkai Yokoshu CD-ROM, 2004 Nen 9 Gatsu 1 Nichi Hakko, vol. 53(2), pp. 5386-5387 2W14.
Jin'ich Inokuchi, et al.: "2-gata Tonyobyo no Insulin Teikosei ni Kakawaru Ganglioside GM3 no Kino", Dai 23 Kai the Japanese Society of Carbohydrate Research Nenkan Yoshishu, 2002 Nen 7 Gatsu 25 Nichi Hakko, p. 70.
M. Gavella, et al.: "Lipid-Bound Sialic Acid in Diabetes", Horm. Metabol. Res., 1989, vol. 21(5), pp. 280-281.
Dong Hoon Kwak, et al.,: "Decreases of ganglioside GM3 in streptozotocin-induced diabetic glomeruli of rats", Life Sciences, Mar. 14, 2003, vol. 72(17), pp. 1997-2006.
Tagami, et al., J. Biol. Chem., vol. 277, pp. 3085-3092, 2002.
Kabayama, et al., Glycobiology, vol. 15, pp. 21-29. 2005.
Inokuchi J., "Insulin resistance as a membrane microdomain disorder", Biol. Pharm. Bull., 29(8):1532-1537 (2006).

* cited by examiner

*Primary Examiner* — Jacob Cheu
(74) *Attorney, Agent, or Firm* — Morgan, Lewis & Bockius LLP

(57)   ABSTRACT

Disclosed is a simple method for detecting a pathological condition of an insulin-resistant disease, particularly type-2 diabetes. The method comprises quantifying the ganglioside GM3 in a blood sample separated from a living body. More specifically, the method comprises the following steps (a) to (c): (a) separating a plasma or serum from the blood collected from a human; (b) quantifying the ganglioside GM3 in the plasma or serum; and (c) comparing the quantified ganglioside GM3 level to the mean ganglioside GM3 level determined in blood samples from healthy volunteers.

11 Claims, 3 Drawing Sheets

METHOD FOR DETECTION OF DISEASE HAVING INSULIN-RESISTANT CONDITIONS

CROSS REFERENCE TO RELATED APPLICATIONS

This application is a U.S. National Phase Application of International Application Number PCT/JP2007/061246, filed May 29, 2007, which claims the benefit of Japanese Patent Application No. 2006-149328, filed May 30, 2006, each of which is incorporated by reference in its entirety.

TECHNICAL FIELD

The present invention relates to a method for detection of a disease having insulin-resistant conditions, particularly type 2 diabetes and more particularly, to a method for detection of type 2 diabetes which comprises assaying the ganglioside GM3 level in blood.

BACKGROUND ART

Diabetes is called a contemporary national affliction as the central core of lifestyle-related diseases, and there is a pressing need to develop methods for its prevention and treatment. While the mechanism of onset of the disease has not yet been elucidated, it is considered that two pathological conditions of deficiency of insulin as a hormone for lowering the blood glucose level (impaired insulin secretion) and impaired insulin action (insulin resistance) are complicated. Diabetes is generally classified into (1) type 1 caused by the destruction of insulin-secreting pancreatic β cells and requiring continuous replenishment of insulin; (2) type 2 associated with deficient secretion of insulin or deteriorated action of insulin; (3) other types of diabetes induced by specific causes; (4) gestational diabetes, and the like.

Type 1 diabetes is one of autoimmune diseases, and also clinically termed insulin dependent diabetes. In this type, pancreatic β-cells that secrete insulin are attacked and destroyed by the autoimmune system. Insulin is a hormone that acts to lower blood glucose levels by absorbing glucose into the cells. Where insulin secretion is suppressed, blood glucose levels are elevated and cells become glucose deficient. Then, the cells cannot maintain their life activities when such a glucose-deficient state persists to cause impairments of various organs, loss of sight and foot necrosis. The model mouse of type 1 diabetes is known in the art, and studies on the therapy of type 1 diabetes have also been advanced using the mouse model (for example, see Science, 2003, Nov. 14, 302 (5648): 1223-7).

From the clinical point of view, Type 2 diabetes is often called as insulin independent diabetes and develops due to impaired insulin secretion in the pancreatic β-cells and insulin resistance. Which one of impaired insulin secretion and insulin resistance is strongly associated with type 2 diabetes differs depending upon respective cases or the process of each case, and both are often complicated. In normal subjects, glucose is absorbed after a meal and when blood sugar levels begin to elevate, insulin is secreted immediately in response the elevated glucose level, whereas in the impaired insulin secretion this response is lacking and insulin is secreted late after the increase in blood sugar levels.

Type 2 diabetes develops from relative deficiency of insulin action. In many cases, systemic insulin resistance is observed and, recently the relation of obesity, overeating or lack of exercise to the systemic insulin resistance, which was earlier only empirically understood, has been elucidated on a molecular level. Insulin resistance is defined as "a condition in which responsiveness of an insulin-sensitive cell or organ to insulin on a physiological level is reduced" and is positioned at the uppermost stream in the pathophysiology of type 2 diabetes.

Adipose tissue was simply understood as a mere energy reservoir so fax but has been recently recognized as a major endocrine organ in living subjects, actually producing various physiologically active substances, which are collectively referred to as adipocytokine. In particular, it was made clear that dysfunction of adipocytes associated with an overaccumulation of visceral fat in obesity, namely, abnormality of adipocytokine secretion (e.g., oversecretion of inflammatory cytokine TNFα, reduced secretion of adiponectin, etc.) induces insulin resistance, which plays an important role as various causes of pathological conditions of type 2 diabetes and arteriosclerotic diseases. Recently, it has been found that macrophages infiltrate and invade the adipose tissue to secrete inflammatory cytokine in white adipose tissue and as a result, induce insulin resistance, which draws attention to pathological physiology of myeloid cells latently present in adipose tissue.

Insulin receptor is localized to caveolae microdomain of cell membrane which is formed by accumulating a lipid group having a high phase transition temperature such as gangliosides (sphingoglycolipids), sphingomyelins, cholesterol, etc. A major ganglioside in adipose tissue is termed GM3. It is reported that the expression of ganglioside GM3 and its synthase gene is significantly up-regulated in adipose tissue stimulated with TNFα as well as in adipose tissue of typical obese diabetic model animals (Tagarni, et al., J. Biol. Chem., Vol. 277, 3085-3092, 2002). In addition, the relationship between the insulin metabolic signaling defect and a loss of insulin receptors in the microdomains due to an overaccumulation of GM3 is also reported (Kabayama et al., Glycobiology, Vol. 15, 21-29, 2005).

On the other hand, presently hematological diagnosis of type 2 diabetes is generally made by using blood glucose, HbA1c and glycoalbumin levels, etc. as indicators. The blood glucose level is a value obtained by measuring a glucose concentration in blood. HbA1c means a glycated protein in which glucose binds to hemoglobin in erythrocyte and is measured as the ratio of glycated protein to the total hemoglobin. HbA1c is considered to reflect the blood glucose control condition during the previous one or two months from the erythrocyte life span (120 days).

In addition, glycoalbumin (GA) is considered to reflect the blood glucose control condition from the previous two weeks to one month because the half-life period of albumin is 17 days. When compared with HbA1c, glycoalbumin can be observed more quickly with a larger change and is useful as an indicator to assess therapeutic effects and drug dosage.

In order to accurately assess the condition of type 2 diabetes, however, it is required to combine these measurement methods.

Furthermore, Harashima, et al. discloses the method of diagnosis by expression analysis of various genes in Published Japanese Patent Application KOKAI No. 2005-253434. However, in the case of this method, the diagnosis requires the expression analysis of various genes and cannot be made in a simple way.

DISCLOSURE OF THE INVENTION

Under the circumstances described above, it has been desired to develop a method for detection of type 2 diabetes in a simpler and accurate manner.

The present inventor made extensive studies on the method for detection of type 2 diabetes and as a result, has found that diseases having insulin-resistant conditions, particularly type 2 diabetes can be detected in a simple manner by quantifying ganglioside GM3 in blood. The present invention has thus been accomplished. More specifically, the present invention provides the method for detection of diseases having insulin-resistant conditions, the method for predicting a risk of developing diseases having insulin-resistant conditions, and so on, which are described below.

(1) A method for detection of a disease having insulin-resistant conditions, which comprises quantifying ganglioside GM3 in a blood sample separated from a living subject. Herein, the term "disease having insulin-resistant conditions" is used to mean a disease that insulin metabolic signaling is impaired to have an insulin independent condition, and includes, for example, type 2 diabetes, hyperlipidemia, hypertension, obesity, etc. Hereinafter the "disease having insulin-resistant conditions" is sometimes simply referred to as "insulin-resistant diseases."

(2) The method for detection according to (I) above, wherein the blood sample separated from a living subject is a blood sample separated from a human.

(3) The method for detection according to (2) above, wherein the blood sample separated from a human is human plasma or serum.

(4) The method for detection according to (1) above, which comprises:

(a) a step of separating plasma or serum from human blood collected;

(b) a step of quantifying ganglioside GM3 in the plasma or serum separated; and, (c) a step of comparing the quantified GM3 level to a mean ganglioside GM3 level in blood samples derived from healthy volunteers.

(5) The method for detection according to (4) above, wherein said quantification of ganglioside GM3 is performed by high performance liquid chromatography (HPLC), high performance thin layer chromatography (HPTLC), high performance liquid chromatography-mass spectrometry (LC-MS) or gas chromatography-mass spectrometry (GC-MS).

(6) The method for detection according to any one of (1) through (5) above, wherein said disease having insulin-resistant conditions is type 2 diabetes, hyperlipemia, hypertension or obesity.

(7) The method for detection according to any one of (1) through (5) above, wherein said disease having insulin-resistant conditions is type 2 diabetes.

(8) A method for predicting a risk of developing a disease having insulin-resistant conditions, which comprises monitoring changes in ganglioside GM3 level in a blood sample collected from a subject.

(9) The method according to (8) above, wherein said blood sample collected from a subject is human plasma or serum.

(10) The method according to (9) above, which comprises:

(a) a step of separating plasma or serum from human blood collected;

(b) a step of quantifying ganglioside GM3 in the plasma or serum separated; and, (c) a step of comparing the quantified GM3 level to a normal ganglioside GM3 level in the blood sample from the subject.

(11) The method according to (10) above, wherein said quantification of ganglioside GM3 is performed by high performance liquid chromatography (HPLC), high performance thin layer chromatography (HPTLC), high performance liquid chromatography-mass spectrometry (LC-MS), gas chromatography-mass spectrometry (GC-MS) or enzyme linked immunosorbent assay (ELISA) using an anti-GM3 antibody.

(12) The method according to (8) above, wherein a blood sample is regularly collected from the subject and changes in the ganglioside GM3 level in the blood sample collected are monitored.

(13) The method according to any one of (8) through (12) above, wherein said disease having insulin-resistant conditions is type 2 diabetes, hyperlipemia, hypertension or obesity.

(14) The method according to any one of (8) through (12) above, wherein said disease having insulin-resistant conditions is type 2 diabetes.

(15) A kit for detecting a disease having insulin-resistant conditions, comprising a ganglioside as the standard substance.

BRIEF DESCRIPTION OF THE DRAWINGS

FIG. 2A shows the results obtained by monitoring the correlation of GM3 level to GA level in plasma from healthy volunteers.

FIG. 2B shows the results obtained by monitoring the correlation of GM3 level to GA level in plasma from patients with type 2 diabetes.

BEST MODE FOR CARRYING OUT THE INVENTION

1. Summary of Invention

Figure 1:
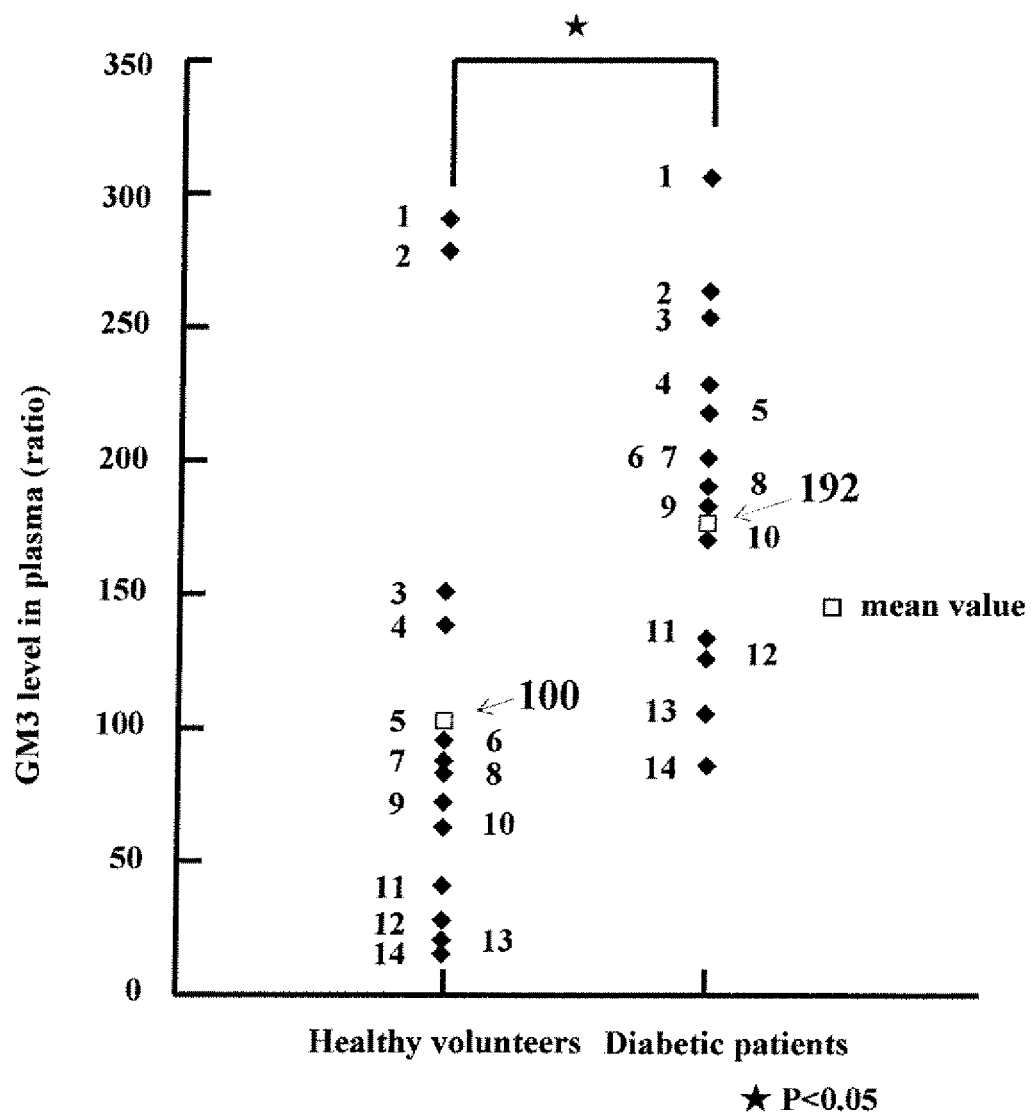
FIG. 1 shows the results obtained by quantifying the GM3 level in plasma.

Presently, hematological diagnosis of type 2 diabetes is made by the measurements of blood glucose, HbA1c and glycoalbumin levels, etc. The present inventor found that markedly up-regulated expression of ganglioside GM3 was observed in type 2 diabetic/obese animal models, when compared to normal animals, and the increase of GM3 could be a potential cause of insulin resistance. In other words, it is suggested that GM3 is involved in lifestyle-related diseases having insulin-resistant conditions, e.g., type 2 diabetes, hyperlipidemia, hypertension, obesity, etc. Based on this finding, gangliosides were analyzed in human plasma and the results revealed that the ganglioside GM3 level was significantly increased. From the results, the novel method for diagnosis of diseases having insulin-resistant conditions, particularly type 2 diabetes has been developed.

More specifically, it is known that ganglioside GM3 as the main component, GD3, GD1a, GM2, GT1b and the like are present in plasma or serum free of blood cell components (Arch. Biochem. Biophys., Vol. 238, 388-400, 1985; Eur. J. Biochem., Vol. 181, 657-662). It is also reported that the level of gangliosides in plasma or serum tends to be increased in autoimmune diseases (Sera et al., J. Neurological Sciences, Vol. 52, 143-148, 1982) or gastric cancer (J. Clin. Lab. Anal., Vol. 3, 301-306, 1989) but any report has not been made to date on gangliosides in patients with type 2 diabetes. In addition, the origin of plasma or serum gangliosides was suggested to be from hematopoietic cells such as liver, macrophages, etc. (Bergelson, Immunology Today, Vol. 16, 483-486, 1995) but it was not clear. Therefore, it was very unclear whether an up-regulated expression of ganglioside GM3 in adipocytes or adipose tissues in a state of obesity and insulin resistance could be detected in a blood sample. Under such circumstances, the present inventor has found that ganglioside GM3 is increased in a higher level and selectively among the ganglioside molecules in blood, in diseases having insulin-resistant conditions, especially in plasma from the patient with human type 2 diabetes. The inventor has further found that the increase of ganglioside GM3 level in plasma from the patient with human type 2 diabetes is not correlated to parameters of hyperglycemia and is therefore useful as a novel method for diagnosis from a new angle, which enables to detect the pathological conditions of complicated metabolic syndrome including type 2 diabetes. The present invention has thus been accomplished. Hereinafter, the present invention is described in detail, focusing on type 2 diabetes as a target example.

2. Method for Detection/Diagnosis of Insulin-Resistant Diseases

First, the present invention provides a method for detection of diseases having insulin-resistant conditions, in particular, type 2 diabetes, which comprises quantifying ganglioside GM3 in a blood sample separated from a living subject. Gangliosides collectively refer to sphingoglycolipids containing sialic acid residues, and are components of mammalian cell walls. It is known that GM3 is present most abundantly as the ganglioside in plasma, followed by GD3, GD1a, GM2. GT1b, etc. (Senn, et al., Eur. J. Biochem., 181, 657-662, 1989). According to the present invention, insulin-resistant diseases are detected by using the blood level of GM3 as an indicator. Insulin-resistant diseases include type 2 diabetes, hyperlipidemia, hypertension, obesity, and so on. The method is particularly effective for detection of type 2 diabetes complicated by hyperlipidemia.

The method for diagnosis of the present invention is not limited only to human but applicable also to a mammal such as cat, rabbit, sheep, dog, monkey, horse, bovine, etc. However, the method for diagnosis targets lifestyle-related diseases and the method for detection of the present invention covers diagnosis especially for human. In this case, a blood sample separated from human is used, preferably, human plasma or human serum is used as a blood sample for the diagnosis.

More specifically, the present invention provides the method for detection of diseases having insulin-resistant conditions, particularly type 2 diabetes, which comprises:

(a) a step of separating plasma or serum from human blood collected;

(b) a step of quantifying ganglioside GM3 in the plasma or serum separated; and, (c) a step of comparing the GM3 level quantified to a mean ganglioside GM3 level in blood samples derived from healthy volunteers.

Herein, the term "human" is used to refer to both healthy volunteers and subjects. By comparing the results obtained from both with one another, it can be diagnosed if one suffers from a disease having insulin-resistant conditions, particularly type 2 diabetes. The term "subject" refers to a target subject on whom the diagnosis of the present invention is made, and includes patients suffering from a disease having insulin-resistant conditions, particularly type 2 diabetes, and patients suspected of having type 2 diabetes.

The term "mean ganglioside GM3 level in blood samples derived from healthy volunteers" can be determined by extracting healthy volunteers living in a specific area such as the region or country at random and measuring ganglioside GM3 levels in blood from these healthy volunteers. In general, the mean ganglioside GM3 level in blood samples from healthy volunteers falls within the range of 3.0 to 6.5 nmol/ml. Accordingly, diagnosis can be made by using this numerical value as an indicator to show if a subject is a patient suffering from a disease having insulin-resistant conditions, particularly type 2 diabetes, or a patient suspected of having type 2 diabetes.

First, plasma or serum is separated from human blood collected at the step (a) described above. Plasma or serum can be separated from blood samples in any conventional manner known to one skilled in the art, for example, using the methods described in Rinsho-Kensa-Gijutsu (Laboratory Test Techniques), 3rd edition (authored by Takashi Kanno and Nobuyoshi Matsuda, published by Igaku-Shoin, Ltd), such as a vacuum blood collection method or a syringe blood collection method. Specifically, whole blood is collected in an EDTA-added blood collection tube, the tube is invert to ensure mixing and then centrifuged at 1,500×g for 10 minutes, whereby plasma can be separated from whole blood. Serum can also be obtained by collecting whole blood in a blood collection tube containing a serum separator, inverting the tube for mixing, allowing the tube to stand for 20 minutes at room temperature, centrifuging as described above and collecting the supernatant. Since pretreatment of the blood sample to be measured provides measurements with higher sensitivity and accuracy, it is preferred to pre-treat the blood sample in an appropriate manner prior to the measurements. The pretreatment includes, for example, centrifugation, deproteinization with an organic solvent or the like, extraction with an organic solvent, partition with an acid or base, use of aminopropyl column, etc.

Next, ganglioside GM3 in the plasma or serum separated at the step (a) is quantified at the step (b). Quantification of ganglioside GM3 is not particularly limited thereto but can also be performed by, e.g., high performance liquid chromatography (HPLC), high performance thin layer chromatography (HPTLC), high performance liquid chromatography-mass spectrometry (LC-MS), gas chromatography-mass spectrometry (GC-MS) or enzyme linked immunosorbent assay (ELISA) using an anti-GM3 antibody. In the present invention, high performance thin layer chromatography (HPTLC) is particularly advantageous.

Ganglioside GM3 in plasma or serum can be quantified, for example, by (1) purifying the ganglioside fraction from plasma or serum, and (2) developing the ganglioside fraction by, e.g., high performance thin layer chromatography, to determine the ganglioside GM3 level.

For purifying the ganglioside fraction from plasma or serum, known methods can be used. Such known methods include the method of Ladisch, et al. (Anal. Biochem., Vol. 146, 220-231, 1985; Methods in Enzymology, Vol. 138, 300-306, 1987). More specifically, the ganglioside fraction can be purified from plasma or serum by the method described in Example, which will be later described.

The ganglioside fraction can also be developed on high performance thin layer chromatography to separate into the respective components. In plasma, ganglioside GM3 as the main component, GD3, GD1a, GM2, GT1b and the like are present, which can be separated by, for example, spotting on a plate for high performance thin layer chromatography manufactured by Merck, Inc., and developing at room temperature using a developing solvent known to one skilled in the art, e.g., chloroform: methanol: 0.2% calcium chloride in a proportion of 55:45:10 (v/v) or 50:35:8 (v/v). The spots of the components detected after development can be quantitatively determined, using a densitometer, e.g., a Flying-Spot Scanner manufactured by Shimadzu Corporation, or an image analyzer. In the present invention the method using a densitometer is preferred.

At the step (c), the GM3 level quantified at the step (b) is then compared to a mean ganglioside GM3 level in blood samples from healthy volunteers. The mean ganglioside GM3 level in blood samples from healthy volunteers is within the range of 3.0 to 6.5 nmol/ml; when the level exceeds the upper limit, it can be diagnosed that a subject suffers from insulin-resistant diseases, e.g., type 2 diabetes, or it is highly likely that one would suffer from these diseases in the future.

3. Method of Predicting a Risk of Developing Insulin-Resistant Diseases

Next, the present invention provides a method of predicting a risk of developing an insulin-resistant disease, particularly type 2 diabetes, by monitoring changes in the ganglioside GM3 level in blood samples taken from subjects.

The method for detection of insulin-resistant diseases described above involves a method of detecting insulin-resistant diseases, particularly type 2 diabetes, by comparing to the ganglioside GM3 level in blood from healthy volunteers. However, expression levels of various genes, proteins, etc. vary between individuals. Accordingly, taking into account such differences between individuals, it may be more accurate to judge a risk of developing insulin-resistant disease, particularly type 2 diabetes, or to judge if a subject suffers from insulin-resistant disease, particularly type 2 diabetes, by regularly measuring the ganglioside GM3 level in his or her own blood and monitoring changes in the ganglioside GM3 level in blood, rather than comparing to the ganglioside GM3 level in blood from healthy volunteers. According to this embodiment, changes in the ganglioside GM3 level in his or her own blood are monitored to predict any risk of developing insulin-resistant diseases, particularly type 2 diabetes.

The ganglioside GM3 level in blood can be quantified by the method described above. According to the present invention, the ganglioside GM3 level in blood is monitored regularly (e.g., every 3 months, every 6 months, every year); when the ganglioside GM3 level in blood is increased by at least 10%, 20%, 30%, 40% or 50% than the normal level, there is a risk of onset of insulin-resistant diseases, particularly type 2 diabetes, or it can be presupposed that a subject suffers from insulin-resistant diseases, particularly type 2 diabetes.

Herein, where there is a risk of developing, e.g., type 2 diabetes or it is presupposed that a subject suffers from type 2 diabetes, other methods for diagnosis of type 2 diabetes may also be used for an integrated diagnosis, by which it can be diagnosed whether or not the subject suffers from type 2 diabetes.

By such a method of predicting onset risk of insulin-resistant diseases, the risk of developing insulin-resistant diseases, particularly type 2 diabetes, can be detected more easily at an earlier stage, which enables one to prevent the onset of type 2 diabetes.

4. Kit for Detecting Insulin-Resistant Diseases, Particularly Type 2 Diabetes The present invention further provides a kit for detecting insulin-resistant diseases, particularly type 2 diabetes, characterized by using the method described above. The kit of the present invention may comprise GM3, GD3, GD1a, GM2 and GT1b as the standard substances, in addition to written instructions for use. The kit may further contain other gangliosides such as GM1, sialylparagloboside, etc. The kit may also contain a plate for high performance thin layer silica gel chromatography and a stock solution (chloroform, methanol, calcium chloride aqueous solution, etc.) as a developing solvent.

Example

Hereinafter the present invention is described in detail with reference to EXAMPLE.

Blood was collected from healthy volunteers in a healthy volunteer group (n=14) and from type 2 diabetic patients in a patient group with type 2 diabetes (n=14) shown in TABLE 1, who gave written informed consent to ensure that they understood the purpose of this study, and plasma was obtained. Ganglioside fractions were purified by the following procedures, developed on high performance thin layer chromatography and then analyzed.

TABLE 1

Blood glucose, HbA1c and GA levels in plasma from healthy volunteers and type 2 diabetic patients used in this study

|  | Healthy Volunteer (n = 14) | Diabetic Patient Group (n = 14) |
|---|---|---|
| Blood glucose level (mg/dl) | 111 ± 13 | 211 ± 27 |
| HbA1c (%) | 5.0 ± 0.4 | 9.6 ± 1.9 |
| GA level (%) | 14.7 ± 2.4 | 31.5 ± 5.0 |

(mean value ± standard deviation)

Figure 2:
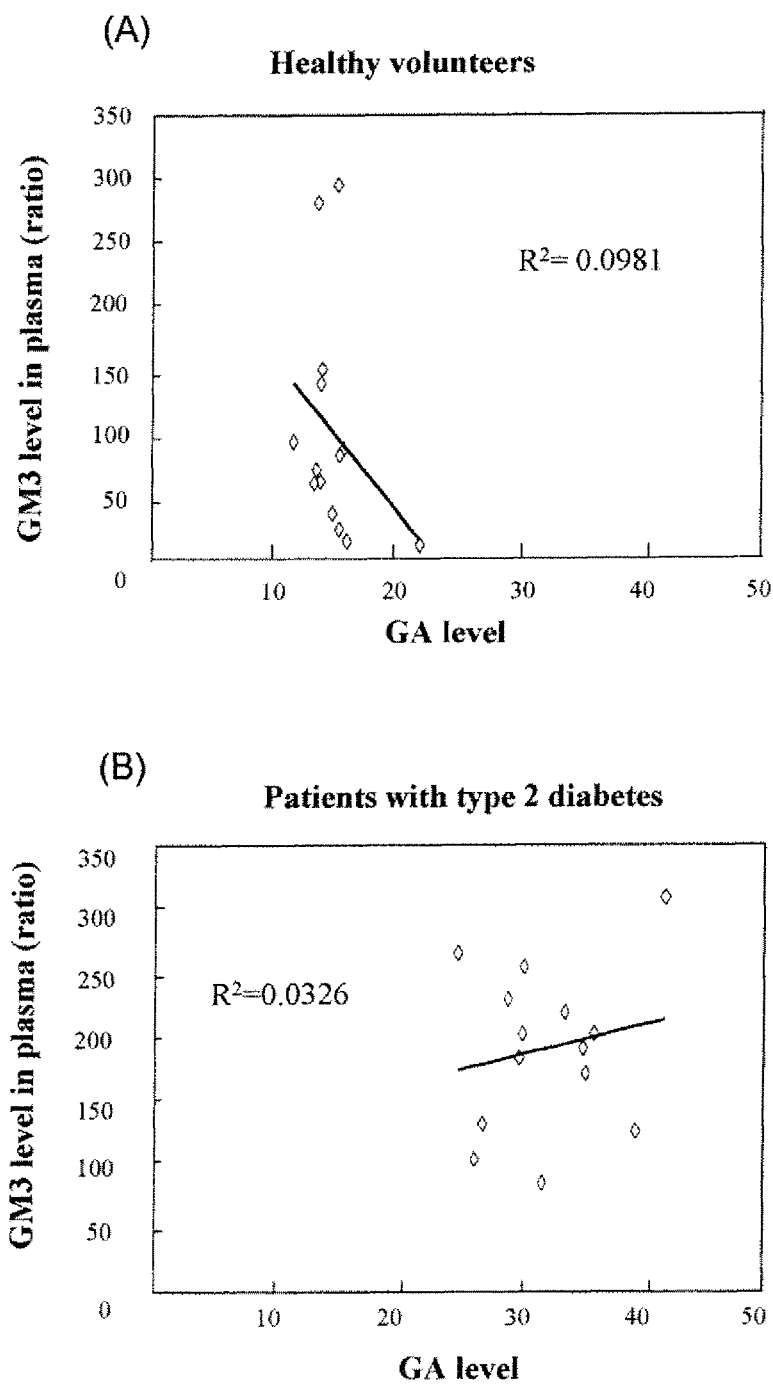
FIG. 2 shows the results obtained by monitoring the correlation of GM3 level to GA level in plasma.

TABLE 1 presents blood glucose, HbA1c and GA levels in samples from healthy volunteers and type 2 diabetic patients who were analyzed for plasma GM3 in FIGS. 1 and 2.

First, ethylenediamine tetraacetate (LUTA) was added to the collected blood. After mixing, the blood was centrifuged at 1500×g and the supernatant was collected to obtain plasma.

Next, 100% ethanol was added to the plasma in a final concentration of 70%. The mixture was centrifuged at 1,000 rpm for 5 minutes and the supernatant was recovered. Then, 10-fold volume of 70% ethanol was again added to the precipitate, followed by incubation at 70° C. for 10 minutes. Similarly, the supernatant was recovered by centrifugation at 1,000 rpm for 5 minutes. The supernatant was combined with the previous extract and the mixture was evaporated to dryness under nitrogen using a rotary evaporator to give the total extract.

Gangliosides were purified by the method of Ladisch, et al. (Anal. Biochem., Vol. 146, 220-231, 1985; Methods in Enzymology, Vol. 138, 300-306, 1987).

Specifically, 6 ml of diisopropyl ether/butanol (3:2) was added to the total extract obtained, followed by ultrasonication for a minute. After 3 ml of 50 mM NaCl was added, the mixture was vigorously stirred (30 seconds×2). Following centrifugation at 1,200 rpm for 5 minutes, the organic solvent phase was removed. After 6 ml of diisopropyl ether/butanol (3:2) was again added to the aqueous phase, the mixture was vigorously stirred as described above and centrifuged to remove the organic solvent phase. To the remaining aqueous phase, 5 ml of 50 mM NaCl was added and the whole solution was added to Sep-Pak (registered trademark) C18 (reversed phase chromatography) attached to a glass syringe, followed by desalting with 40 ml of purified water. Elution was sequentially performed using 10 ml of methanol and 10 ml of chloroform/methanol (1:1) in this order. The eluate was concentrated using an evaporator to prepare the ganglioside fraction.

The resulting ganglioside fraction was developed by spotting the total volume of tissue corresponding to 0.2 g onto a HPTLC plate. Chloroform/methanol/0.5% $CaCl_2$ (60:40:9) was used as a developing solvent and orcinol-sulfuric acid reagent (120° C., 10 minutes) was used as its color developing reagent. After detection, the GM3 level was quantified by a densitometer. The results are shown in FIG. 1.

As illustrated in FIG. 1, the GM3 level as the major ganglioside in plasma was quantified, which showed a significantly higher level in the diabetic patient group than in the healthy volunteer group. On the other hand, no significant change was observed with the other ganglioside molecules GD3, GD1a, GM2, GT1b, etc. on the HPTLC plate. It was thus revealed that the GM3 level in plasma was significantly high in lifestyle-related diseases such as type 2 diabetes, etc., as compared to healthy volunteers. Accordingly, the GM3 level in plasma, which is significantly high in the patients with type 2 diabetes, is a novel marker for type 2 diabetes.

Next, correlation of each of the GA levels to the GM3 levels was studied within each group of the healthy volunteer group and the type 2 diabetic patient group. The results are shown in FIG. 2.

As shown in FIG. 2, the correlation was low in any of the healthy volunteer group and the type 2 diabetic patient group. No correlation of the blood glucose level to the GM3 level was observed either in the healthy volunteer group or in the type 2 diabetic patient group. These results revealed that the ganglioside GM3 level in plasma showed significantly high values in the type 2 diabetic patients but there was no correlation to the GA or blood glucose level as a parameter of hyperglycemia. It was thus made clear that the measurement of GM3 level in patients with type 2 diabetes is useful as a novel method for detection which enables to detect complicated metabolic syndrome from a new angle.

The foregoing results revealed that the GM3 level in serum was significantly increased in the group of patients with uncontrolled type 2 diabetes (HbAlc: 9.6±1.9, GA level: 31.5±5.0) as shown in TABLE 1 and therefore, the group of patients with less severe type 2 diabetes was monitored. In this case, comparison was made in each of the "healthy volunteers," "type 2 diabetes," "hyperlipidemia" and "type 2 diabetes+hyperlipidemia" groups, as shown in following Table 2.

TABLE 2

|  | Healthy Volunteer | Diabetes | Hyperlipidemia | Diabetes + Hyperlipidemia |
|---|---|---|---|---|
| GM3 (µg/mL) | 5.7 ± 2.5 | 7.7 ± 4.1 | 8.0 ± 2.3 | 8.9 ± 3.4 |
| Blood glucose level (mg/dL) | 99 ± 10 | 142 ± 33 | 98 ± 7 | 151 ± 46 |
| HbAlc (%) | 5.3 ± 0.3 | 7.4 ± 1.6 | 5.2 ± 0.4 | 7.3 ± 1.0 |
| HOMA-R level | 1.1 ± 0.5 | 1.3 ± 0.6 | 1.6 ± 0.9 | 3.0 ± 2.1 |

The GM3, blood glucose, HbAlc and HOMA-R (measure of insulin resistance) levels in serum from the "healthy volunteers," "type 2 diabetes," "hyperlipidemia" and "type 2 diabetes+hyperlipidemia" groups are shown in TABLE 2.

As a result, a tendency to increase the GM3 level in serum was observed in the type 2 diabetes group (HbAlc: 7.4±1.6, GA level: 21±5) but the increase was not significant, and HOMA-R as the measure of insulin resistance was not significantly increased either. In the group of type 2 diabetes hyperlipidemia (HbAlc: 7.3±1.0, GA level: 18±6), HOMA-R was 3.0±2.1 (p=0.03) indicating insulin resistance, and the GM3 level in serum was significantly increased. Further in the hyperlipidemia group, the GM3 level in serum showed an increasing tendency similarly to the type 2 diabetes group but did not show any significant difference from the healthy volunteer group. From these results it was established that the measurement of GM3 level in serum is useful in the group of type 2 diabetes combined with hyperlipidemia showing insulin resistance.

Figure 3:
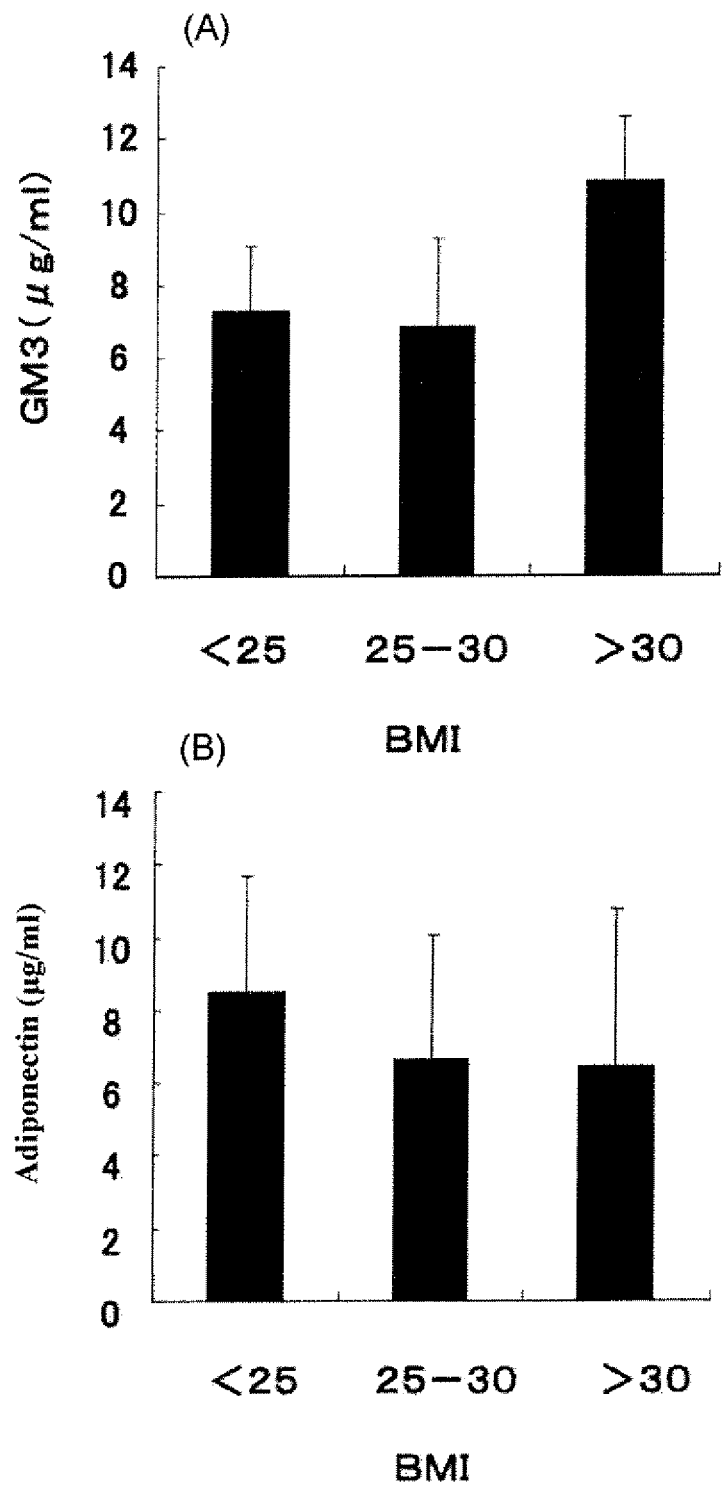
FIG. 3 shows the results obtained by monitoring the correlation of BMI level to GM3 level (A) and to adiponectin level (B). The GM3 level was measured as in FIG. 1 and plasma adiponectin was measured using an adiponectin assay kit (Otsuka Pharmaceutical Co., Ltd., Reagents and Diagnostics Department.

Next, correlation between BMI (Body Mass Index) closely related to the onset or pathological conditions of insulin resistance and the GM3 level in plasma was studied. As a result, an inverse correlation was observed between the BMI level and the adiponectin level, as shown in FIG. 3, and the GM3 level in plasma was clearly high in the diabetic group having a higher BMI level (BMI: >30). It was suggested also from these results that GM3 is useful for the detection/diagnosis of metabolic syndrome accompanied by obesity, which develops insulin resistance.

INDUSTRIAL APPLICABILITY

According to the present invention, insulin-resistant diseases, particularly type 2 diabetes, can be diagnosed in a simple manner using blood samples, which can be easily collected from the living organism, using conventionally available measuring devices.

Further, according to the present invention, a risk of developing insulin-resistant diseases, particularly type 2 diabetes, can be easily predicted by regularly collecting blood samples from subjects, measuring the GM3 level in blood and monitoring changes in the ganglioside GM3 level in blood.

By the detection method of the present invention, insulin resistance, which is a condition common to various lifestyle-related diseases, can be detected and can thus be contributed to strategy for a clinically effective treatment of lifestyle-related diseases including type 2 diabetes, based on the finding of a new pathological mechanism.

The invention claimed is:

1. A method for detection of a disease selected from the group consisting of type 2 diabetes and type 2 diabetes combined with hyperlipidemia, wherein said type 2 diabetes group having a Body Mass Index level greater than 30, which comprises:
    separating plasma or serum from human blood collected;
    quantifying ganglioside GM3 in the plasma or serum separated; and,
    comparing the GM3 level quantified to a mean ganglioside GM3 level in blood samples derived from healthy volunteers, thereby detecting the disease.

2. The method for detection according to claim 1, wherein said quantification of ganglioside GM3 is performed by high performance liquid chromatography (HPLC), high performance thin layer chromatography (HPTLC), high performance liquid chromatography-mass spectrometry (LC-MS), gas chromatography-mass spectrometry (GC-MS) or enzyme linked immunosorbent assay (ELISA) using an anti-GM3 antibody.

3. The method according to claim 1, wherein said disease is type 2 diabetes.

4. A method for predicting a risk of developing a disease selected from the group consisting of type 2 diabetes and type 2 diabetes combined with hyperlipidemia, wherein said type 2 diabetes group having a Body Mass Index level greater than 30, which comprises:
    separating plasma or serum from human blood collected;
    quantifying ganglioside GM3 in the plasma or serum separated;

comparing the GM3 level quantified to a normal ganglioside GM3 level in blood samples from healthy volunteers; and monitoring changes in the ganglioside GM3 level, thereby predicting the risk.

5. The method according to claim 4, wherein said quantification of ganglioside GM3 is performed by high performance liquid chromatography (HPLC), high performance thin layer chromatography (HPTLC), high performance liquid chromatography-mass spectrometry (LC-MS), gas chromatography-mass spectrometry (GC-MS) or enzyme linked immunosorbent assay (ELISA) using an anti-GM3 antibody.

6. The method according to claim 4, wherein a blood sample is regularly collected from the human and changes in the ganglioside GM3 level in the blood sample collected are monitored.

7. The method according to claim 4, wherein said disease is type 2 diabetes.

8. The method of claim 1, wherein the disease is type 2 diabetes combined with hyperlipidemia.

9. The method of claim 1, wherein the disease is a diabetic group having a Body Mass Index level greater than 30.

10. The method of claim 4, wherein the disease is type 2 diabetes combined with hyperlipidemia.

11. The method of claim 4, wherein the disease is a diabetic group having a Body Mass Index level greater than 30.

* * * * *